United States Patent [19]

Fischer et al.

[11] Patent Number: 4,892,686

[45] Date of Patent: Jan. 9, 1990

[54] PROCESS FOR THE PREPARATION OF 1-NITROANTHRAQUINONE

[75] Inventors: Walter Fischer, Reinach; Tibor Somlo, Birsfelden, both of Switzerland

[73] Assignee: Ciba-Geigy Corporation, Ardsley, N.Y.

[21] Appl. No.: 275,238

[22] Filed: Nov. 22, 1988

[30] Foreign Application Priority Data

Dec. 3, 1987 [CH] Switzerland ............... 4722/87

[51] Int. Cl.$^4$ .............................................. C07C 50/18
[52] U.S. Cl. .................................................. 552/253
[58] Field of Search ......................................... 260/369

[56] References Cited

U.S. PATENT DOCUMENTS

| | | | |
|---|---|---|---|
| 3,907,841 | 9/1975 | Dürholz et al. | 260/396 |
| 3,994,932 | 11/1976 | Twanura et al. | 260/369 |
| 4,176,125 | 11/1979 | Matsuura et al. | 260/369 |
| 4,335,050 | 6/1982 | Delavarenne et al. | 260/369 |

OTHER PUBLICATIONS

Chemical Abstract, vol. 55; 21836f.
Synthesis of Polycyclines, vol. 26; (1978), pp. 2579-2581.

Primary Examiner—Richard L. Raymond
Assistant Examiner—Raymond Covington
Attorney, Agent, or Firm—Kevin T. Mansfield; Edward McC. Roberts

[57] ABSTRACT

A process for the preparation of 1-nitroanthraquinone by oxidising 1-nitro-5,8,11,12-tetrahydroanthraquinone with oxygen, inorganic peroxo compounds or metal oxides.

27 Claims, No Drawings

PROCESS FOR THE PREPARATION OF 1-NITROANTHRAQUINONE

The present invention relates to a novel process for the preparation of 1-nitroanthraquinone by reaction of 5-nitro-1,4-naphthoquinone with butadiene to give 1-nitro-5,8,11,12-tetrahydroanthraquinone and oxidation thereof to 1-nitroanthraquinone.

1-Nitroanthraquinone is an important intermediate for the synthesis of anthraquinone dyes. For this reason it is always desirable to provide novel processes for the preparation of this intermediate. In contrast to the unsubstituted 5,8,11,12-tetrahydroanthraquinone, which can be converted into anthraquinone by simple air oxidation, the presence of the nitro group in 1-nitro-5,8,11,12-tetrahydroanthraquinone complicates its oxidation to 1-nitroanthraquinone.

The present invention relates to a process for the preparation of 1-nitroanthraquinone by (1) reacting 5-nitro-1,4-naphthoquinone with butadiene, (2) oxidising the 1-nitro-5,8,11,12-tetrahydroanthraquinone so obtained to 1-nitroanthraquinone, and (3) isolating the 1-nitroanthraquinone, which process comprises reacting in step (2) 1-nitro-5,8,11,12-tetrahydroanthraquinone (a) with oxygen, an inorganic peroxo compound or a metal oxide as oxidising agent to 1-nitro-5,8-dihydroanthraquinone, and then (b) oxidising this intermediate to 1-nitroanthraquinone with one of the above oxidising agents.

This process makes it possible to prepare 1-nitroanthraquinone in simpler and cheaper manner than has so far been possible. The intermediate is obtained in very high purity (up to 99%) and in high yield (up to 95%), so that its further processing to 1-nitroanthraquinone is greatly facilitated. The process can be carried out on an industrial scale without difficulty.

The process of this invention is based on the oxidation of the 1-nitrotetrahydroanthraquinone obtained by conventional Diels-Alder reaction with oxygen, inorganic peroxo compounds or metal oxides [reaction step (2)]. This oxidation gives 1-nitroanthraquinone via the novel intermediate 1-nitro-5,8-dihydroanthraquinone.

This intermediate and a process for the preparation thereof, as well as a process for the preparation of 1-nitroanthraquinone starting from said intermediate consitute, further objects of the present invention.

In the process of this invention, the oxidation of the tetrahydro compound gives 1-nitroanthraquinone via the novel dihydro compound. For reasons of selectivity, it is important that this oxidation should be carried out in two steps [(2)(a) and (2)(b)]. First, the tetrahydro compound is converted almost completely into the dihydro comound [(2)(a)], and then the further oxidation to the 1-nitroanthraquinone is carried out [(2)(b)].

After step (2)(a), the dihydro compound can be isolated in high yield. On account of its high purity, it can be used, for example, direct for the further oxidation to 1-nitroanthraquinone [(2)(b)]. As a time-saving procedure, the isolation of the dihydro compound can be dispensed with and step (2)(b) can then follow directly after step (2)(a).

In order to increase the purity of the intermediate, step (2)(b) can be followed by an oxidising aftertreatment of the 1-nitroanthraquinone, for example with an oxidising acid. Aqueous nitric acid, usually having a concentration of 65%, has proved to be an especially effective oxidising acid for this aftertreatment.

In step (2)(a) of the process of this invention, the tetrahydro compound is oxidised, for example, with (atmospheric) oxygen in a solvent. The conventional air inlet systems are used for the oxidation, with aerating stirrers being especially preferred. If desired, oxidation is effected in the presence of a base. Depending on its basicity, it is preferred to use different organic and/or inorganic solvents. If a weak base is used, for example an alkali metal carbonate or basic alumina or preferably an alkali metal acetate, particularly suitable solvents are aprotic, polar solvents such as ketones and ethers. Examples of preferred solvents are methyl ethyl ketone, acetone and diethylene glycol dimethyl ether. If it is desired to use a strong base such as an alkali metal hydroxide, then suitable solvents are protic, polar solvents such as water and an alcohol such as methanol or ethanol, or an aqueous solution of such an alcohol. In this case, the 1-nitro-5,8,11,12-tetrahydroanthraquinone must also be added to the solution of the strong base in one of the cited solvents.

The oxidation of the tetrahydro compound with (atmospheric) oxygen can also be carried out by means of two variants, the preferred embodiments of which are oxidation in the presence of sodium acetate in dimethylene glycol dimethyl ether, and oxidation in the presence of sodium hydroxide in water or methanol.

If an inorganic peroxo compound is used as oxidising agent in step (2), it is in particular a perborate, peroxide, persulfate, peroxodisulfate or a mixture of hydrogen peroxide and tetraboric acid. The peroxo compound is preferably used in the form of an alkali metal salt. A solvent is used for this type of oxidation, preferably an organic solvent such as nitrobenzene or acetic acid or a mixture thereof. In some cases it can be advantageous to carry out the dehydrogenation of the tetrahydro compound in the presence of an acid such as sulfuric acid or of a base such as sodium acetate, or of an inorganic salt such as sodium bicarbonate or magnesium oxide.

The oxidation of the tetrahydro compound with sodium perborate or a mixture of hydrogen peroxide and sodium tetraborate in glacial acetic acid and/or nitrobenzene, as well as the oxidation with sodium or potassium persulfate in glacial acetic acid in the presence of sulfuric acid or sodium or potassium acetate, constitute preferred embodiments of the oxidation with peroxo compounds.

A preferred metal oxide which is suitable for use in step (2) of the process of this invention is manganese dioxide. The oxidation with this oxide is preferably carried out in an organic solvent such as benzene, toluene, xylene, cumene, cymene, methylene chloride, carbon tetrachloride, acetonitrile, ethyl acetate, nitrobenzene, acetone, glacial acetic acid, tetrahydrofuran, dioxane or dichlorobenzene. Nitrobenzene is especially preferred.

In partial steps (2)(a) and (2)(b) it is preferred to use the same oxidising agent. It is, however, also possible to use different oxidising agents in these steps, for example air in step (2)(a) and manganese dioxide in step (2)(b).

Especially if (atmospheric) oxygen is used in steps (2)(a) and (2)(b), it can be advantageous to initiate the oxidation in the presence of a customary radical former such as azobisisobutyronitrile.

In a particularly preferred embodiment of the process of this invention, the tetrahdro compound is oxidised with oxygen in the presence of sodium hydroxide in water as solvent, without isolation of the dihydro compound, and the product is subjected to an aftertreatment with nitric acid, affording 98.5% 1-nitroanthraquinone in a yield of 93.5%.

The reaction temperatures in steps (2)(a) and (2)(b) can vary within a wide range. Depending on the oxidising agent and the solvent employed, the reaction temperatures in step (2)(a) are normally in the range from 5° to 100° C., whereas somewhat higher temperatures are as a rule required for step (2)(b), preferably in the range from 20° to 160° C. The optional aftertreatment of the 1-nitroanthraquinone with an oxidising acid or a Fe(III) salt following step (2)(b) can be carried out at the boiling temperature of the reaction mixture.

The isolation of the 1-nitroanthraquinone is effected in conventional manner, for example by precipitation and filtration, decantation or centrifugation.

The invention is illustrated in more detail by the following Examples.

EXAMPLE 1

320 parts of nitrobenzene and 81.2 parts of 5-nitro-1,4-naphthoquinone are charged to a 0.5 liter flask with bottom outlet. The flask is evaluated and 26 parts of 1,3-butadiene are introduced into the closed system, resulting in slight overpressure. The mixture is heated to 80°–85° C. and stirred for 3 hours at this temperature, in the course of which the overpressure must be substantially removed. Excess butadiene (ca. 4 parts) is then removed by distillation.

A 1 liter flask is then charged with 320 parts of glacial acetic acid and 286 parts of sodium perborate containing 4 parts of water of crystallisation, and the solution of the butadiene adduct in nitrobenzene is run in at 55°–60° C.

The temperature of the mixture is then raised from 75° to 80° C. and the mixture is stirred for 5 hours at this temperature. The nitrobenzene solution is then washed 3 times with 400 parts of water, the water is removed as an azeotrope, 50 parts of nitric acid (65%) and 0.5 part of sodium nitrite are added, and the batch is refluxed for 1½ hours (105° C.).

The mixture is cooled to 5° C., the crystals are filtered with suction, washed with a small amount of isopropanol and water, and dried at 100° C. under vacuum, affording 80 parts of 1-nitroanthraquinone in about 99% purity.

EXAMPLE 2

A 1½ liter flask equipped with aerating stirrer is charged with 800 parts of diethylene glycol dimethyl ether. Then 203.2 parts of 5-nitro-1,4-naphthoquinone are added, the flask is evacuated, and 65 parts of 1,3-butadiene are introduced into the closed system, resulting in slight overpressure. The mixture is stirred for 3 hours at 80°–85° C., excess butadiene is removed by distillation, and the mixture is cooled to 20° C.

Then 16 parts of sodium acetate containing 3 parts of water of crystallisation and 4 parts of azobisisobutyronitrile are added, air is introduced with the aerating stirrer while stirring vigorously, and the temperature is kept at 27°–30° C. (if necessary by gentle cooling). After some hours, all the tetrahydro compound has been converted to the dihydro compound. By diluting the mixture with water it is possible to isolate the pure 1-nitro-5,8-dihydroanthraquinone in almost quantitative yield.

EXAMPLE 3

A 750 ml flask equipped with aerating stirrer is charged with 400 parts of diethylene glycol dimethyl ether. Then 101.6 parts of 5-nitro-1,4-naphthoquinone are added, the flask is evacuated, and 32.5 parts of 1,3-butadiene are introduced into the closed system. The mixture is stirred for 3 hours at 80°–85° C. When all the 5-nitro-1,4-naphthoquinone has been converted, excess butadiene is removed by distillation and the mixture containing the tetrahydro compound is cooled to 20° C. Then 8 parts of sodium acetate containing 3 parts of water of crystallisation and 2 parts of azobisisobutyronitrile are added and air is introduced while stirring vigorously with the aerating stirrer. The reaction temperature is kept at 27°–30° C. (if necessary by gentle cooling). After 4 to 6 hours all the 1-nitro-5,8,11,12-tetrahydroanthraquinone has been converted to the 1-nitro-5,8-dihydro-anthraquinone.

The mixture is subsequently acidified with 8 parts of 65% nitric acid, the flask is evacuated to ca. 35 mm Hg and the water of reaction is removed as an azeotrope (distillation temperature: 63°–65° C.). The reaction mixture is cooled to 20° C., then 16 parts of potassium acetate and 2 parts of azobisisobutyronitrile are added, and air is blown into the reaction mixture by the aerating stirrer until no more 1-nitro-5,8-dihydroanthraquinone can be detected. If this is the case, then 2 parts of sodium nitrite and 100 parts of 65% nitric acid are added dropwise, whereupon the temperature rises from 25° C. to ca. 65° C. The mixture is then heated to reflux (105° C.) and stirred under reflux until no more gas evolves.

The mixture is subsequently cooled to 5° C., the crystals are filtered with suction, washed with a small amount of isopropanol and water, and dried at 100° C. under vacuum, affording 94 parts of 1-nitroanthraquinone in ca. 99% purity.

EXAMPLE 4

A 1 liter flask equipped with aerating stirrer is charged with 400 parts of diethylene glycol dimethyl ether (diglyme). Then 101.6 parts of 5-nitro-1,4-naphthoquinone are added and 1,3-butadiene is introduced at 80°–85° C. until all the nitroanthraquinone has been converted to the Diels-Alder adduct. Excess butadiene is then expelled with nitrogen, the mixture is cooled to 20° C., 8 parts of sodium acetate containing 3 parts of water of crystallisation and 2 parts of azobisisobutyronitrile are added, and air is blown in by the aerating stirrer while stirring vigorously. Initially the reaction is somewhat exothermic, and by gentle cooling the reaction temperature is kept for 2 hours at 20°–23° C., then for a further 2 hours at 23°–27° C., and for yet a further 2 hours at 27°–30° C.

When all the 1-nitro-5,8,11,12-tetrahydroanthraquinone has been converted to the 1-nitro-5,8-dihydroanthraquinone, 8 parts of 65% nitric acid and 300 parts of glacial acetic acid are added and then 173 parts of sodium perborate are added, in portions, at 70°–75° C. Thereafter the mixture is heated to 75°–80° C. and stirred at this temperature until no more 1-nitro-5,8-dihydroanthraquinone can be detected.

The reaction mixture is diluted with water, the crystals are filtered with suction, washed with water and extracted by boiling in 200 parts of 65% nitric acid until no more gas evolves. The mixture is then diluted with 200 parts of water and cooled to room temperature. The crystals are isolated by suction filtration, washed with water, and dried at 100° C. under vacuum, affording 110 parts of 1-nitroanthraquinone in ca. 99% purity.

EXAMPLE 5

With stirring, 4.78 g (31.1 mmol) of $NaBO_3.4H_2O$ are dissolved in 10 ml of glacial acetic acid at 100° C. Then 2.0 g (7.78 mmol) of 1-nitro-tetrahydroanthraquinone are added in portions over 20 minutes. After stirring for 1 hour at 100° C., a further 3.58 g (23.3 mmol) of $NaBO_3.4H_2O$ are added. After stirring for a further hour at 100° C., the mixture is cooled, diluted with 10 ml of water, and briefly stirred. The product is isolated by filtration, washed repeatedly with water and then dried at 140° C. under vacuum. The yield of 1-nitroanthraquinone is 1.75 g (89%). Melting point: 230°–232° C.

The reaction proceeds in the same manner using 1-nitro-5,8-dihydroanthraquinone as starting material.

EXAMPLE 6

5 g (24.61 mmol) of 5-nitro-1,4-naphthoquinone are dissolved in 40 ml of nitrobenzene. With stirring, butadiene is introduced over 10.5 hours at 40° C. Nitrogen is blown in for 1 hour and then 8.55 g (98.45 mmol) of manganese dioxide are added. After 6 hours at 40° C., the mixture is heated to 160° C. and filtered hot. The residue is washed with hot nitrobenzene. The combined mother liquors are cooled to 25° C., whereupon pure 1-nitroanthraquinone precipitates in a yield of 4.37 g (70%). The precipitate is isolated by filtration and dried. The melting point is 235°–238° C.

Elemental analysis of $C_{14}H_7NO_4$ (mol.wt. 253.21): calculated: C 66.41, H 2.79, N 5.53, O 25.28%. found: C 66.45, H 2.74, N 5.66, O 25.21%.

In corresponding manner, 65% of product is obtained when using toluene as solvent, 79% when using acetonitrile, and 63% when using ethyl acetate.

EXAMPLE 7

15 g (58.8 mmol) of 1-nitro-5,8-dihydroanthraquinone and 20.45 g of manganese dioxide are stirred at reflux for 2 hours in 150 ml of methylene chloride. After addition of 15 g of anhydrous sodium sulfate, the mixture is filtered hot and the residue is repeatedly extracted by boiling in methylene chloride. Concentration of the mother liquors by evaporation gives 13.58 g (91%) of crude 1-nitroanthraquinone (melting point: 225°–230° C.), which can be recrystallised from toluene (melting point: 228°–232° C.).

Elemental analysis of $C_{14}H_7NO_4$ (mol.wt. 253.21): calculated: C 66.41, H 2.79, N 5.53, O 25.28%. found: crude: C 66.46, H 2.84, N 5.50, O 25.04%. pure: C 66.55, H 2.80, N 5.56, O 25.17%.

EXAMPLE 8

With stirring, 0.38 g (3.89 mmol) of potassium acetate is dissolved in 3.5 ml of glacial acetic acid at 70° C. (bath temperature). Then 2.10 g (7.77 mmol; 4 equivalents) of potassium persulfate are added, whereupon a white suspension forms. Then 0.5 g (1.94 mmol) of 1-nitro-5,8,11,12-tetrahydroanthraquinone is added. After stirring for 30 minutes at 70° C., the bath temperature is raised to 90° C. After a further 2.5 hours at 90° C., the mixture is cooled and poured into 25 ml of water. The precipitate is isolated by filtration, washed with water and dried. The residue is extracted 3 times by boiling in toluene. Partial concentration of the mother liquors and subsequent cooling and filtration yield 0.42 g (86%) of 1-nitroanthraquinone with a melting point of 225°–230° C.

EXAMPLE 9

A mixture of 1.85 g (7.77 mmol) of sodium persulfate, 0.48 g of a 3% solution of concentrated $H_2SO_4$ in glacial acetic acid and 3.5 ml of glacial acetic acid is stirred at 70° C. Then 0.50 g (1.94 mmol) of 1-nitro-5,8,11,12-tetrahydroanthraquinone is added. The reaction temperature is then raised to 120° C. over 15 minutes. After 4 hours at 120° C., the reaction mixture is cooled and pured into 25 ml of water. The precipitate is isolated by filtration, washed with water and dried in a drying oven. Recrystallisation from toluene gives 0.29 g (59%) of 1-nitroanthraquinone.

Elemental analysis of $C_{14}H_7NO_4$ (mol.wt. 253.21) calculated: C 66.41, H 2.79, N 5.53, O 25.28%. found: C 65.98, H 3.16, N 5.48, O 25.23%.

EXAMPLE 10

500 parts of methanol and 80 parts of 50% sodium hydroxide solution are mixed in a 1 liter sulfonating flask equipped with aerating stirrer and the solution is cooled to 5° C. With efficient stirring, 51.4 parts (0.2 mol) of 1-nitro-5,8,11,12-tetrahydroanthraquinone are added in portions at 5°–10° C. The suspension immediately turns dark blue. When the addition of nitro-tetrahydroanthraquinone is complete, the temperature is raised to 30° C. while vigorously blowing in air with the aerating stirrer and then kept at 30° to 35° C. (if necessary by gentle cooling).

In the course of the aeration, the consistency and colour of the suspension changes: first it becomes green and viscous, then anthracite grey and less viscous and, after about 3 hours, the colour suddenly changes to orange/beige. Stirring is continued for 1 hour at 35° C., then the pH of the suspension containing the dihydro compound is adjusted to 6 with sulfuric acid. Subsequently 300 parts of water are added and the methanol is removed from the mixture by distillation. The brownish red suspension is then filtered and the filter residue is washed free of salt with water and dried at 70°–80° C. under vacuum, affording about 50 parts of a reddish brown substance that melts with decomposition at ca. 200° C. With stirring, this substance is added to 200 ml of 65% nitric acid and the suspension is refluxed, whereupon nitrous gases evolve. The mixture is refluxed until the evolution of gas ceases (ca. 2 hours), then the suspension is cooled to ca. 5° C. The lustrous yellow crystals are filtered with suction and washed with water until neutral and dried at 100° C. under vacuum, affording 48 parts of 1-nitroanthraquinone in 98.5% purity (melting point: 232° C.), i.e. 93.5% of theory (based on 1-nitro-5,8,11,12-tetrahydroanthraquinone).

EXAMPLE 11

A 1 liter glass pressure reactor is charged with 160 parts of 50% aqueous sodium hydroxide, 112 parts of 50% aqueous potassium hydroxide and 750 parts of water. The mixture is cooled to 10° C. and, at this temperature, 163.2 parts of technical 1-nitro-5,8,11,12-tetrahydroanthraquinone (100%) are added in portions as 94–95% product. The batch is stirred for 2 hours at 10° C., whereupon the suspension turns dark green. Subsequently the mixture is warmed to 30° C., the gas space in the reactor is flushed with oxygen and oxygen is blown in at 1 bar. With efficient stirring, temperature (30°–32° C.) and oxygen overpressure (1 bar) are kept constant, such that over 1 hour 1 mol of oxygen is taken up per mol of nitro-tetrahydroanthraquinone and then the oxygen uptake decreases. During the oxygen uptake, the colour of the mixture changes from dark green to beige-brown via bluish-green and pale grey. In this phase the suspension of the nitrodihydroanthraquinone forms. While maintaining the oxygen pressure, the reaction mixture is heated over 1 hour to 100° C. and stirred for 1 hour at this temperature, whereupon the oxygen uptake increases to 1 mol of oxygen per educt.

The reaction mixture is thereafter cooled to 25° C., the overpressure is removed, and the suspension is rinsed with 1000 parts of water in a 2½ liter flask. The pH of the suspension in the flask is adjusted to 5.5 with ca. 200 parts of 70% sulfuric acid. The suspension is then heated to 100° C., stirrer for 15 minutes at 100° C., cooled to 25° C. over 2 hours, and filtered. The filter residue is washed with water and dried at 80°-90° C. under vacuum, affording 148 parts of crude 1-nitroanthraquinone (consisting of ca. 93% of 1-nitroanthraquinone and 3 to 4% of 1-nitrodihydroanthraquinone), corresponding to a yield of 90% of theory (without taking into account the content of 1-nitrodihydroanthraquinone).

The crude product can be further processed direct to intermediates and dyes.

If it is desired to obtain very pure 1-nitroanthraquinone, then the crude product is treated with 400 ml of 65% nitric acid as described in Example 10. In this case the yield of pure 1-nitroanthraquinone is 138 parts (99% purity), i.e. 90% of theory, based on 1-nitro-5,8,11,12-tetrahydroanthraquinone.

EXAMPLE 12

A 1 liter glass pressure reactor is charged with 600 parts of toluene and 122 parts of technical 5-nitro-1,4-naphthoquinone (100%) as ca. 93% product. The reactor is blanketed with nitrogen and 57.6 parts of butadiene are introduced under pressure. The mixture is then heated in the closed system to 80° C. and stirred for 4 hours at this temperature. The pressure falls from a maximum of 3.5 to 4 bar to ca. 3 bar at the conclusion of the reaction. The mixture is cooled, the pressure in the reactor removed over a cooling trap, and excess butadiene is distilled at 400 mbar from the autoclave into the cooling trap. At a distillation temperature of 80° C., a total amount of 336 parts of butadiene/toluene is present in the cooling trap, with a butadiene content of ca. 6%. Then the residual toluene is removed with steam, such that at the conclusion of the steam distillation the suspension of 1-nitro-5,8,11,12-tetrahydroanthraquinone in 750 parts of water is free from toluene. The suspension is then run at 10° C. into a mixture of 160 parts of 50% aqueous sodium hydroxide and 50% aqueous potassium hydroxide. Further processing as described in Example 11 gives 138 parts of pure (99%) 1-nitroanthraquinone, i.e. 90% of theory, based on 5-nitro-1,4-naphthoquinone.

EXAMPLE 13

With stirring, 0.38 part (3.89 mmol) of potassium acetate is dissolved in 5 parts of glacial acid at 90° C. Then 2.1 parts (7.77 mmol; 4 equivalents) of potassium persulfate are added, whereupon a white suspension forms. Then 1.0 g (3.84 mmol) of nitrodihydroanthraquinone is added. After stirring for 3 hours at 90° C., the mixture is cooled and poured into 50 ml of water. The precipitate is isolated by filtration, washed with water, and dried. The residue is extracted by boiling 3 times in toluene. Partial concentration of the mother liquors and subsequent cooling and filtration give 0.84 part (86% of theory) of 1-nitroanthraquinone with a melting point of 228°-230° C.

What is claimed is:

1. A process for the preparation of 1-nitroanthraquinone by (1) reacting 5-nitro-1,4-naphthoquinone with butadiene, (2) oxidising the 1-nitro-5,8,11,12-tetrahydroanthraquinone so obtained to 1-nitroanthraquinone, and (3) isolating the 1-nitroanthraquinone, which process comprises reacting in step (2) 1-nitro-5,8,11,12-tetrahydroanthraquinone (a) with oxygen, as inorganic peroxide compound or a metal oxide as oxidising agent and isolating 1-nitro-5,8-dihydroanthraquinone, and then (b) oxidising this intermediate to 1-nitroanthraquinone with one of the above oxidising agents.

2. A process according to claim 1, which comprises subjecting the 1-nitroanthraquinone to an aftertreatment with an oxidising acid after step (2)(b).

3. A process according to claim 2, wherein nitric acid is used as oxidising acid.

4. A process according to claim 1, wherein the oxidation in step (2)(a) is carried out with oxygen in a solvent and in the absence or presence of a base.

5. A process according to claim 4, wherein the base is an alkali metal acetate, alkali metal bicarbonate and/or a basic aluminium oxide.

6. A process according to claim 5, wherein the base is an alkali metal acetate.

7. A process according to claim 5, wherein the oxidation is carried out in methyl ethyl ketone, acetone or diethylene glycol dimethyl ether as solvent.

8. A process according to claim 4, wherein the base is an alkali metal hydroxide.

9. A process according to claim 8, wherein the oxidation is carried out in water, an alcohol or a mixture thereof as solvent, the 1-nitro-5,8,11,12-tetrahydroanthraquinone being added to a solution of an alkali metal hydroxide in one of the cited solvents.

10. A process according to claim 4, wherein the oxidation is carried out with oxygen in the presence of sodium acetate in diethylene glycol dimethyl ether.

11. A process according to claim 4, wherein the oxidation is carried out with oxygen in the presence of sodium hydroxde in water or methanol.

12. A process according to claim 1, wherein the oxidation is carried out in step (2)(a) with an alkali metal perborate, alkali metal peroxide, alkali metal persulfate or ammonium peroxodisulfate or with a mixture of hydrogen peroxide and tetraboric acid, optionally in the presence of an acid, a base, or of an inorganic salt in a solvent.

13. A process according to claim 12, wherein the oxidation is carried out in glacial acetic acid or nitrobenzene or a mixture thereof as solvent.

14. A process according to claim 12, wherein the oxidation is carried out with sodium perborate or with a mixture of hydrogen peroxide and sodium tetraborate in glacial acetic acid or nitrobenzene or a mixture thereof as solvent.

15. A process according to claim 12, wherein the oxidation is carried out with sodium or potassium persulfate in glacial acetic acid in the presence of sulfuric acid or sodium or potassium acetate.

16. A process according to claim 1, wherein the oxidation is carried out with manganese dioxide.

17. A process according to claim 16, wherein the oxidation is carried out in benzene, toluene, xylene, cumene, cymene, methylene chloride, carbon tetrachloride, acetonitrile, ethyl acetate, nitrobenzene, acetone, glacial acetic acid, tetrahydrofuran, dioxane or dichlorobenzene as solvent.

18. A process according to claim 16, wherein the oxidation is carried out in nitrobenzene.

19. A process according to claim 1, wherein the same oxidising agent is used in steps (2)(a) and (2)(b).

20. A process according to claim 1, wherein the oxidation is initiated in steps (2)(a) and (2)(b) with a radical former.

21. A process according to claim 1, wherein the oxidation in steps (2)(a) and (2)(b) is carried out with oxygen in the presence of sodium hydroxide in water, without isolation of the 1-nitro-5,8-dihydroanthraquinone obtained as intermediate, and subsequently subjecting the resultant 1-nitroanthraquinone to an optional after-treatment with nitric acid.

22. A process according to claim 21, wherein 1-nitroanthraquinone is obtained in greater than 95% purity.

23. A process according to claim 1, wherein step (2)(a) is carried out in the temperature range from 5° to 100° C.

24. A process according to claim 1, wherein step (2)(a) is carried out in the temperature range from 20° to 160° C.

25. 1-Nitro-5,8-dihydroanthraquinone.

26. A process for the preparation of 1-nitro-5,8-dihydroanthraquinone, which comprises reacting 1-nitro-5,8,11,12-tetrahdroanthraquinone after step (2)(a) according to claim 1 and isolating the reaction product.

27. A process for the preparation of 1-nitroanthraquinone, which comprises reacting 1-nitro-5,8-dihydroanthraquinone after step (2)(b) according to claim 1 and isolating the reaction product.

* * * * *